United States Patent
Reinerth et al.

(10) Patent No.: US 9,617,386 B2
(45) Date of Patent: Apr. 11, 2017

(54) PROCESS FOR THE PRODUCTION OF POLYIMIDE AND POLYAMIC ESTER POLYMERS

(71) Applicant: Fujifilm Electronic Materials U.S.A., Inc., North Kingstown, RI (US)

(72) Inventors: William A. Reinerth, Riverside, RI (US); Sanjay Malik, Attleboro, MA (US); Binod B. De, Attleboro, MA (US)

(73) Assignee: Fujifilm Electronic Materials U.S.A., Inc., N. Kingstown, RI (US)

( * ) Notice: Subject to any disclaimer, the term of this patent is extended or adjusted under 35 U.S.C. 154(b) by 13 days.

(21) Appl. No.: 14/280,827

(22) Filed: May 19, 2014

(65) Prior Publication Data

US 2014/0343223 A1    Nov. 20, 2014

Related U.S. Application Data

(60) Provisional application No. 61/824,529, filed on May 17, 2013.

(51) Int. Cl.

| C08G 63/02 | (2006.01) |
|---|---|
| C08G 73/10 | (2006.01) |
| C09D 179/08 | (2006.01) |
| C08K 5/1535 | (2006.01) |
| C08K 5/101 | (2006.01) |
| C08K 5/06 | (2006.01) |
| C08K 5/07 | (2006.01) |

(52) U.S. Cl.
CPC ..... *C08G 73/1071* (2013.01); *C08G 73/1014* (2013.01); *C08G 73/1032* (2013.01); *C08G 73/1039* (2013.01); *C08G 73/1067* (2013.01); *C08K 5/06* (2013.01); *C08K 5/07* (2013.01); *C08K 5/101* (2013.01); *C08K 5/1535* (2013.01); *C09D 179/08* (2013.01)

(58) Field of Classification Search
None
See application file for complete search history.

(56) References Cited

U.S. PATENT DOCUMENTS

| 3,856,752 A | 12/1974 | Bateman et al. |
|---|---|---|
| 3,983,092 A | 9/1976 | Bateman et al. |
| 3,993,630 A | 11/1976 | Darmory et al. |
| 4,122,076 A | 10/1978 | Jablonski et al. |
| 4,558,117 A | 12/1985 | Nakano et al. |
| 4,684,714 A | 8/1987 | Lubowitz et al. |
| 4,689,378 A | 8/1987 | Chaudhari et al. |
| 4,734,482 A | 3/1988 | Tamai et al. |
| 4,775,734 A | 10/1988 | Goel |
| 4,923,954 A * | 5/1990 | Klobucar ........... C08G 73/1032 528/125 |
| 5,025,084 A | 6/1991 | Dobinson et al. |
| 5,047,487 A | 9/1991 | Camargo et al. |
| 5,397,847 A | 3/1995 | Harris et al. |
| 5,412,065 A | 5/1995 | Amone et al. |
| 5,478,915 A | 12/1995 | Amone et al. |
| 5,606,013 A | 2/1997 | Chaudhari et al. |
| 5,618,655 A | 4/1997 | Davidson |
| 5,637,772 A | 6/1997 | Malik et al. |
| 5,643,998 A | 7/1997 | Nakano et al. |
| 5,914,385 A | 6/1999 | Hayashi et al. |
| 5,945,251 A | 8/1999 | Davidson |
| 6,303,744 B1 | 10/2001 | Meador et al. |
| 7,312,281 B2 | 12/2007 | Sheehan et al. |
| 8,039,579 B2 | 10/2011 | McManus et al. |
| 2002/0182536 A1 | 12/2002 | Kamada et al. |
| 2004/0235992 A1 | 11/2004 | Okada et al. |
| 2006/0083928 A1 | 4/2006 | Miyagawa et al. |
| 2007/0269665 A1 | 11/2007 | Shimoohsako et al. |
| 2009/0069508 A1 | 3/2009 | Poe et al. |
| 2009/0253805 A1 | 10/2009 | Hoyle et al. |
| 2009/0306329 A1 | 12/2009 | Hasegawa |
| 2013/0059985 A1 | 3/2013 | Kutsuzawa |

FOREIGN PATENT DOCUMENTS

| CN | 103289090 | 9/2013 | ............. C08G 73/10 |
|---|---|---|---|
| EP | 0 317 754 | 5/1989 | ............. C08G 73/10 |
| FR | 2 609 037 | 7/1988 | ............. C08G 73/10 |
| JP | 57-108158 | 7/1982 | ............. C08L 79/08 |
| JP | 61-254543 | 11/1986 | ............. C07C 93/14 |
| JP | 2008/081713 | 4/2008 | ........... G01R 23/173 |
| TW | 201200542 | 1/2012 | ............. C08G 73/10 |
| WO | WO 99/58579 | 11/1999 | ............... C08F 6/00 |
| WO | WO 2010/111755 | 10/2010 | |
| WO | WO 2012/007499 | 1/2012 | ............... F01D 9/02 |

OTHER PUBLICATIONS

International Search Report and Written Opinion of the International Searching Authority for International Application No. PCT/US14/38562 by Examiner Lee W. Young dated Sep. 30, 2014 (10 pages).

Supplemental European Search Report for EP Application Serial No. 14 79 8630 by Examiner Christof Friedrich dated Jan. 24, 2017 (7 pages).

\* cited by examiner

*Primary Examiner* — Ana Woodward

(74) *Attorney, Agent, or Firm* — Fish & Richardson P.C.

(57) ABSTRACT

This disclosure relates to a process of purifying a polymer. The process includes (a) providing an organic solution containing a polyimide or polyamic ester in at least one polar, aprotic polymerization solvent; (b) adding at least one purification solvent to the organic solution to form a diluted organic solution, the at least one purification solvent is less polar than the at least one polymerization solvent and has a lower water solubility than the at least one polymerization solvent at 25° C.; (c) washing the diluted organic solution with water or an aqueous solution to obtain a washed organic solution; and (d) removing at least a portion of the at least one purification solvent in the washed organic solution to obtain a solution containing a purified polyimide or polyamic ester. This disclosure also relates to a process of preparing a film on a semiconductor substrate, as well as related purified polymer solutions, films, and articles.

20 Claims, 1 Drawing Sheet

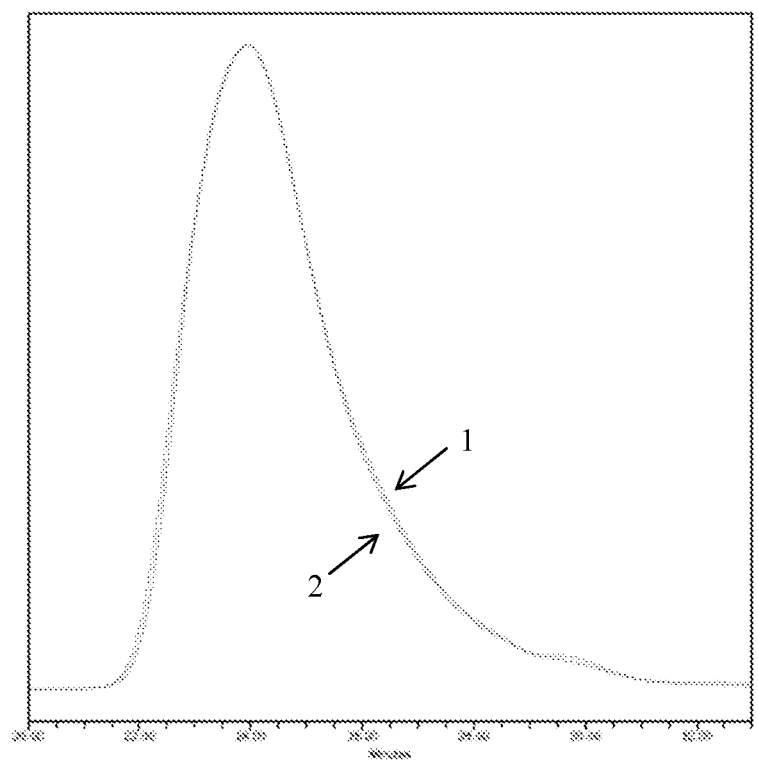

PROCESS FOR THE PRODUCTION OF POLYIMIDE AND POLYAMIC ESTER POLYMERS

CROSS-REFERENCE TO RELATED APPLICATION

The present application claims priority to U.S. Provisional Application Ser. No. 61/824,529, filed on May 17, 2013, the contents of which are hereby incorporated by reference in its entirety.

BACKGROUND

Polyimide polymers have been used for several decades as thermally and chemically resistant materials in a variety of applications. In addition, they have superior mechanical properties which make them valuable for the manufacturing of various electronic devices.

Polyimide (PI) polymers are typically prepared by chemical or thermal treatment of their precursors, polyamic acid (PAA) polymers or polyamic ester (PAE) polymers. While most PAA and PAE polymers are soluble in the polar, aprotic polymerization solvents in which they are synthesized, the resulting PI polymers formed upon imidization are usually insoluble. In many applications, since the PI polymer is not soluble, the PAA or PAE polymer is coated onto a substrate and cured to temperatures in excess of 350° C. to form the PI polymer. In recent advanced applications, coating of a soluble PI polymer is more preferable than coating of its PAA or PAE precursors because of lower required curing temperature and lower film thickness loss due to curing, which results in less stress on the substrate.

In those cases where the PI polymer remains soluble, isolation and purification are accomplished by addition of the polymerization solution to a large amount of a non-solvent. See for example U.S. Pat. Nos. 3,856,752, 4,026,876, 5,252,534, 5,478,915, US20040265731 and US20040235992 which are incorporated by reference. Typical non-solvents are water, low boiling alcohols, such as methanol and 2-propanol, or hydrocarbon solvents such as hexane or toluene. The precipitated polymer is then filtered, washed with an additional large amount of non-solvent and dried under vacuum at elevated temperature. In most cases, in order to obtain a material of sufficient purity, the polymer must be re-dissolved in a solvent and precipitated a second time into a non-solvent. Presence of impurities in PI polymers results in compositions with inferior properties such as mechanical, electrical or chemical resistance. In addition, presence of minute amount of undesired polar aprotic polymerization solvents in the final polymer or compositions from those polymers is undesirable from environmental, safety and health perspective. These methods are also used to isolate PAA and PAE polymers. In this way, conventional processes used to produce PI, PAA and PAE polymers will often generate from 100 kilograms to 500 kilograms of waste for every 1 kilogram of polymer produced. Additionally, using conventional methods, it is exceedingly difficult to reduce the amount of residual solvent to a desired level (e.g., less than 1 wt %) due at least in part to the strong association of the undesired polar aprotic polymerization solvent with the PI, PAA and PAE polymers. Moreover, the excessive amount of polymer handling resulting from multiple precipitations, filtrations and drying steps can further compromise the purity of the polymers from contamination with species such as trace metals.

SUMMARY

This disclosure describes an environmentally-friendly, efficient process for the preparation and purification of soluble polyimide (PI) and polyamic ester (PAE) polymers. This process can significantly reduce the amount of impurities (e.g., residual solvents or metals) in the PI and PAE polymers obtained while significantly reducing the waste generated compared to a conventional precipitation process. The PI and PAE polymers thus obtained have a wide variety of applications such as dielectric and packaging materials for semiconductor devices.

In one aspect, this disclosure features a process of purifying a polymer that includes (a) providing an organic solution containing a polyimide or polyamic ester in at least one polar, aprotic polymerization solvent; (b) adding at least one purification solvent to the organic solution to form a diluted organic solution, the at least one purification solvent is less polar than the at least one polymerization solvent and has a lower water solubility than the at least one polymerization solvent at 25° C.; (c) washing the diluted organic solution with water or an aqueous solution to obtain a washed organic solution; and (d) removing at least a portion of the at least one purification solvent in the washed organic solution to obtain a solution containing a purified polyimide or polyamic ester.

In another aspect, this disclosure features a purified polymer solution obtained by the above process.

In another aspect, this disclosure features a process of preparing a film on a substrate that includes (a) providing an organic solution containing a polyimide or polyamic ester in at least one polar, aprotic polymerization solvent; (b) adding at least one purification solvent to the organic solution to form a diluted organic solution, the at least one purification solvent is less polar than the at least one polymerization solvent and has a lower water solubility than the at least one polymerization solvent at 25° C.; (c) washing the diluted organic solution with water or an aqueous solution to obtain a washed organic solution; (d) removing at least a portion of the at least one purification solvent in the washed organic solution to obtain a solution containing a purified polyimide or polyamic ester; and (e) coating the solution containing a purified polyimide or polyamic ester on a substrate to form a film.

In another aspect, this disclosure features a free-standing film obtained by the process described above.

In still another aspect, this disclosure features an article containing a semiconductor substrate and a film prepared by the process described above on the semiconductor.

BRIEF DESCRIPTION OF DRAWING

FIG. 1 is a graph showing overlay of GPC chromatograms obtained from the polymer in Example 7 and the polymer in Comparative Example 1. Chromatogram 1 was obtained from the polymer in Example 7. Chromatogram 2 was obtained from the polymer in Comparative Example 1.

DETAILED DESCRIPTION

Wherever the term "solvent(s)" is used, if not specifically stated, it refers to either a single organic solvent or a combination of two or more organic solvents.

The current disclosure describes an efficient, environmentally-friendly process for the production of PI and PAE polymers having enhanced purity. In some embodiments, the process described in the current disclosure can avoid precipitation and isolation of the solid polymers, and can result in a purified solution of the desired polymer useful for incorporation into compositions of various types, including thermally- and photochemically-curable compositions.

In some embodiments, this disclosure relates to a process of purifying a polymer. The process can include (a) providing an organic solution containing a polyimide or polyamic ester in at least one polar, aprotic polymerization solvent; (b) adding at least one purification solvent to the organic solution to form a diluted organic solution, the at least one purification solvent is less polar than the at least one polymerization solvent and has a lower water solubility than the at least one polymerization solvent at 25° C.; (c) washing the diluted organic solution with water or an aqueous solution to obtain a washed organic solution; (d) removing at least a portion of the at least one purification solvent in the washed organic solution to obtain a solution containing a purified polyimide or polyamic ester.

Step 1—Process for Forming a Polyimide or Polyamic Ester

In some embodiments, the step of providing an organic solution containing a polyimide or polyamic ester in at least one polar, aprotic polymerization solvent can be performed by forming a polyimide or polyamic ester using appropriate starting reagents in at least one polar, aprotic polymerization solvent without isolating the polyimide or polyamic ester thus obtained.

For example, in the initial step of one embodiment of the process, one or more diamine(s) are combined with one or more tetracarboxylic acid dianhydride(s) in at least one (e.g., two, three, or more) polymerization solvent(s) to form a polyamic acid (PAA) polymer. In one embodiment, the PAA polymer formed is imidized, either chemically or thermally, to form a PI polymer which remains soluble in the polymerization solvent(s). In another embodiment, the PAA polymer is end-capped by use of an appropriate reagent during the polymer synthesis or by using an appropriate agent after the polymer synthesis and prior to imidization. In another embodiment, the PAA polymer formed is esterified to form a PAE polymer which remains soluble in the polymerization solvent(s). Alternatively, in another embodiment, the PAE polymer is formed by combination of a tetracarboxylic half ester with one or more diamines in at least one polymerization solvent(s). In another embodiment, the PAE polymer is end-capped by using an appropriate agent prior to imidization.

In one embodiment of this disclosure, a chemical imidizing agent (e.g., a dehydrating agent) is added to a PAA polymer that catalyzes the ring-closing dehydration process of the polyamic acid groups to form imide functionalities, thereby forming a PI polymer. Examples of suitable dehydrating agents include, but are not limited to, trifluoromethane sulfonic acid, methanesulfonic acid, p-toluenesulfonic acid, ethanesulfonic acid, butanesulfonic acid, perfluorobutanesulfonic acid, acetic anhydride, propionic anhydride, and butyric anhydride. In addition, this dehydration process can be catalyzed by further addition of a basic catalyst. Examples of suitable basic catalysts include, but are not limited to, pyridine, triethylamine, tripropylamine, tributylamine, dicyclohexylmethylamine, 2,6-lutidine, 3,5-lutidine, picoline, 4-dimethylaminopyridine (DMAP) and the like. If used, the basic catalyst employed can be the same as or different from the basic catalyst employed in the end-capping reaction described above.

In some embodiments, the PI polymers of this disclosure remain soluble in the polymerization solvent(s) following imidization. In some embodiments, the PAE polymers of this disclosure remain soluble in the polymerization solvent(s) following esterification and/or polymerization.

Methods to synthesize endcapped and non-endcapped PAA, PI and PAE polymers are well known to those skilled in the art. Examples of such methods are disclosed in U.S. Pat. Nos. 2,731,447, 3,435,002, 3,856,752, 3,983,092, 4,026,876, 4,040,831, 4,579,809, 4,629,777, 4,656,116, 4,960,860, 4,985,529, 5,006,611, 5,122,436, 5,252,534, 5,478,915, 5,773,559, 5,783,656, and 5,969,055, US patent applications US20040265731, US20040235992, and US2007083016, and European patent application EP0317754 A2, the contents of which are hereby incorporated by reference.

The polymerization solvent(s) is generally one or a combination of two or more polar, aprotic solvents. Suitable polar, aprotic solvents include, but are not limited to, dimethylformamide (DMF), dimethylacetamide (DMAc), N-formylmorpholine (NFM), N-methylpyrrolidinone (NMP), N-ethylpyrrolidinone (NEP), dimethylsulfoxide (DMSO), gamma-butyrolactone (GBL), hexamethyl phosphoric acid triamide (HMPT), tetrahydrofuran (THF), methyltetrahydrofuran, 1,4-dioxane and mixtures thereof.

In another embodiment, the reaction mixture for the polymerization, imidization, and/or esterification reaction can also include an additional polymerization co-solvent. Examples of suitable polymerization co-solvents include, but are not limited to 1,2-dimethoxyethane, 1,2-dimethoxypropane, diglyme, triglyme, and tetraglyme. In some embodiments, the polymerization solvents and/or the reaction co-solvents can be water miscible solvents.

Examples of suitable diamines that can be used to prepare a PI or PAE polymer include, but are not limited to, 4,4'-[1,4-phenylene-bis(1-methylethylidene)]bisaniline (DAPI), 2,2-bis(4-[4-aminophenoxy]phenyl)propane (BAPP), 2,2-bis(4-[4-aminophenoxy]phenyl)hexafluoropropane (HFBAPP), 2,2-bis(4-aminophenyl)hexafluoropropane (Bis-A-AF), 4,4'-oxydianiline (ODA), 1,3-phenylene diamine, 1,4-phenylene diamine, 4,4'-methylenedianiline (MDA), 3,4'-oxydianiline, 4,4'-diaminodiphenylsulfone (DDS), 3,3'-diaminodiphenylsulfone, 4,4'-diaminodiphenylsulfide (ASD), 1,3-bis(3-aminophenoxy)benzene (APB-133), 4,4'-methylene-bis(2-chloroaniline), 1,3-bis(aminopropyl)tetramethyldisiloxane, m-tolidine, o-toluidine, 1,4-diaminodurene (DAD), 1,3-diaminomesitylene (DAM) and the diamines mentioned in the US patents and US patent applications referenced above.

Examples of suitable tetracarboxylic acid dianhydrides that can be used to prepare a PI or PAE polymer include, but are not limited to, pyromellitic dianhydride (PMDA), 3,3', 4,4'-benzophenone tetracarboxylic dianhydride (BTDA), 2,2'-bis(3,4-dicarboxyphenyl)hexafluoropropane dianhydride (6FDA), 3,3',4,4'-biphenyl tetracarboxylic dianhydride (BPDA), 4,4'-oxydiphthalic anhydride (ODPA), 5-(2,5-dioxotetrahydrol)-3-methyl-3-cyclohexene-1,2-dicarboxylic anhydride (B-4400), 4,4'-bisphenol A dianhydride (BPADA), 3,3',4,4'-diphenylsulfone tetracarboxylic dianhydride (DSDA) ethylene glycol bis(trimelllitic anhydride) and the tetracarboxylic acid dianhydrides mentioned in the US patents and US patent applications referenced above.

A range of different time, temperature and concentration conditions for the polymerization, imidization and esterification reactions may be suitably employed. Examples of such processes are described in the US patents and US patent applications referenced above. One skilled in the art will understand appropriate conditions to employ for these syntheses.

Step 2—Dilution with Purification Solvent(s)

After the polymerization, imidization, and/or esterification reaction in step 1, the reaction mixture formed in step 1 can be diluted with at least one (e.g., two, three, or more) purification solvent(s) to form a diluted organic solution containing the polyimide or polyamic ester. The purification solvent(s) can be a solvent or combination of two or more solvents which is less polar than the polar, aprotic polymerization solvent(s) and has lower solubility in water than the polymerization solvent(s) employed at 25° C. Without wishing to be bound by theory, it is believed that the two key functions of the purification solvent(s) are to (1) maintain the PI or PAE polymer in solution and (2) form a biphasic mixture with water and/or an aqueous solution containing an additive. In the context of this disclosure, biphasic mixture refers to a mixture containing two distinct and separate phases (e.g., two distinct liquid phases).

In some embodiments, the purification solvent(s) can include an ester, an ether, a ketone, a hydrocarbon optionally substituted by at least one halide (e.g., F, Cl, Br, or I), or a mixture thereof. Examples of suitable purification solvent(s) include, but are not limited to, methyl acetate, ethyl acetate, n-propyl acetate, isopropyl acetate, n-butyl acetate, isobutyl acetate, sec-butyl acetate, cyclohexyl acetate, ethyl lactate, propylene glycol monomethyl ether acetate (PGMEA), tetrahydrofurfuryl acetate, propyl formate, butyl formate, isobutyl formate, pentyl formate, epsilon-caprolactone, diethyl ether, dipropyl ether, dibutyl ether, dicyclohexyl ether, cyclopentyl methyl ether, methyl tert-butyl ether, ethyl tert-butyl ether, anisole, phenyl ethyl ether, diphenyl ether, 1,2-dimethoxypropane, 1,2-dimethoxyethane, 2-butanone, 2-pentanone, 3-pentanone, methyl isobutyl ketone, ethyl isobutyl ketone, methyl isopropyl ketone, cyclopentanone, cyclohexanone, acetophenone, isophorone, mesityl oxide, benzene, toluene, xylene, ethyl benzene, chlorobenzene, 1,2-dichlorobenzene, $\alpha,\alpha,\alpha$-trifluorotoluene, pentane, hexane, heptane, octane, cyclohexane, methylcyclohexane, cyclohexene, and mixtures thereof.

Depending on the solubility characteristics of the PI or PAE polymer, the purification solvent(s) may be used as the sole solvent(s) in the dilution/purification step. However, in some embodiments, in addition to the purification solvent(s), a purification co-solvent(s) may be employed. Purification co-solvents are organic solvents that have a higher (e.g., significantly higher) solubility in water at 25° C. than the purification solvent(s). In general, a purification co-solvent(s) is not used alone but is used in combination with one or more purification solvent(s). In some embodiments, the purification solvents can be water immiscible solvents.

Examples of suitable purification co-solvents include, but are not limited to, acetone, gamma-butyrolactone (GBL), furan, tetrahydrofuran, methyl tetrahydrofuran, tetrahydrofurfuryl methyl ether, 1,4-dioxane, and mixtures thereof. In some embodiments, the purification co-solvents can be water miscible solvents.

Step 3—Washing the Diluted Organic Solution

Once the PI or PAE polymer has been diluted in the purification solvent(s), this diluted organic solution can be subjected to washing with water and/or an aqueous solution containing an additive (e.g., an acid or a base) to obtain a washed organic solution. Without wishing to be bound by theory, it is believed that this step can purify the PI or PAE polymer by removal of the polymerization solvent(s), polymerization by-products, catalysts, residual monomers and other impurities from the polymer-containing organic phase into the aqueous phase.

When an aqueous solution containing an additive is employed in this step, this solution can contain an acid, a base, or additional components, such as chelating agents, in a sufficient concentration to enhance the purity of the PI or PAE polymer by removal of impurities (e.g., polymerization by-products). The concentration of the acid, the base, or other additives in this aqueous solution may range from at least about 0.1 wt % (e.g. at least about 0.3 wt %, at least about 0.5 wt %, or at least about 1 wt %) to at most about 10 wt % (e.g. at most about 8 wt %, at most about 7 wt %, or at most about 5 wt %).

In some embodiments, the washing step can include adding water or an aqueous solution to the diluted organic solution obtained in the dilution step above. In such embodiments, the washing step can include forming a mixture having an organic phase and an aqueous phase (e.g., by allowing the organic phase and the aqueous phase to separate from each other). The washing step can further include removing the aqueous phase. In general, washing the diluted solution can substantially remove the at least one polymerization solvent or another impurity in the diluted organic solution.

In order to improve the effectiveness of the washing step, the diluted organic solution from step 2 containing a PI or PAE polymer and the aqueous washing medium (e.g., water or an aqueous solution) can be mixed by agitation. This agitation may take the form of stirring, shaking, inverting or any other method which permits effective mixing of the organic and aqueous phases.

Following mixing, the mixture can be allowed to stand undisturbed until two distinct and separate phases are formed. Upon the formation of distinct and separate phases, the aqueous phase can be removed and discarded to remove impurities (e.g., a polymerization solvent). Step 3 (and optionally together with step 2, as required) may be repeated any number of times to achieve the desired polymer purity. In some embodiments, the number of aqueous washes is from one to five (i.e., one, two, three, four or five).

The total amount of water and/or aqueous solution containing an additive employed to purify the PI or PAE polymer ranges from about one kilogram to about 80 kilograms of aqueous medium per kilogram of polymer.

A wide range of agitation rate, time, temperature and separation conditions may be employed. Without wishing to be bound by theory, it is believed that an essential aspect of this step is to ensure sufficient mixing of the mixtures to extract significant amounts of the polymerization solvent(s) and other impurities into the aqueous phase followed by phase separation. These conditions may vary depending on the vessel employed for the mixing and separation. In some embodiments, the agitation time is from about 1 minute to about 24 hours (e.g., from about 10 minutes to about 6 hours). In some embodiments, the agitation temperature is from about 10° C. to about 40° C. (e.g., from about 15° C. to about 30° C.). In some embodiments, the separation time is from about 10 minutes to about 24 hours (e.g., from about 15 minutes to about 12 hours). In some embodiments, the separation temperature is from about 10° C. to about 40° C. (e.g., from about 15° C. to about 30° C.).

In some embodiments, when a PI polymer is being formed and purified, the amount of residual polymerization solvent(s) remaining after the final aqueous washing is at most about 1 wt % (e.g., at most about 0.5 wt %) of the weight of the PI polymer. In some embodiments, when a PAE polymer is being formed and purified, the amount of residual polymerization solvent(s) remaining after the final aqueous washing is at most about 5 wt % (e.g., at most about 4 wt %, at most about 3 wt %, at most about 2 wt %, at most about 1 wt %, at most about 0.5 wt %) of the weight of the PAE polymer.

Step 4—Solvent Removal and/or Exchange

After the organic solution containing a PI or PAE polymer is washed by an aqueous medium (e.g., water), at least a portion (e.g., substantially all) of the purification solvent(s) in the organic solution can be removed or exchanged for at least one isolation solvent(s) to obtain a solution containing a purified PI or PAE polymer (i.e., a purified polymer solution).

In some embodiments, at least a portion (e.g., substantially all) of the purification solvent(s) (and essentially all residual water) in the purified polymer solution can be solvent exchanged for an isolation solvent(s). In some embodiments, the isolation solvent(s) is a solvent or combination of two or more solvents whose boiling point is equal to or greater than the purification solvent(s). In certain embodiments, the isolation solvent(s) can be the same as the purification solvent(s) or polymerization solvent(s). In other embodiments, the isolation solvent(s) can be different from the purification solvent(s) or polymerization solvent(s). In some embodiments, the isolation solvent(s) are compatible with various coating and application methods employed in many industrial applications.

In some embodiments, the isolation solvent(s) can include a ketone, an ester, a hydrocarbon, a sulfoxide, an ether, or a mixture thereof. Examples of suitable isolation solvent(s) include, but are not limited to, methyl ethyl ketone (MEK), methyl isobutyl ketone (MIBK), 2-heptanone, cyclopentanone, cyclohexanone, xylene, gamma-butyrolactone, dimethylsulfoxide, propylene glycol monomethyl ether acetate (PGMEA), propylene glycol monomethyl ether (PGME), ethyl lactate (EL) and mixtures thereof.

In some embodiments, the isolation solvent(s) can be first added to the washed, purified organic solution containing a PI or PAE polymer. In such embodiments, the purification solvent(s) can then be removed by evaporation or distillation. In some embodiments, the amount of residual purification solvent(s) remaining after this step can be at most about 2 wt % (e.g., at most about 1 wt %) of the weight of the PI or PAE polymer. Without wishing to be bound by theory, it is believed that adding an isolation solvent(s) have a boiling point higher than that of the purification solvent(s) can facilitate the removal of the purification solvent(s) during distillation.

Without wishing to be bound by theory, it is believed that, in addition to exchanging the purification solvent(s) for the isolation solvent(s), this step also serves to dry the final polymer solution by removing residual water along with the purification solvent(s) (e.g., through distillation).

In some embodiments, after at least a portion (e.g., substantially all) of the purification solvent(s) is exchanged for the isolation solvent(s), the solution containing the PI or PAE polymer can be concentrated to form a solution suitable for coating on a substrate.

In some embodiments, when the isolation solvent(s) is the same as the purification solvent(s), the solvent removal step can be performed by first adding a certain amount of purification solvent(s) into the washed, purified organic solution containing a PI or PAE polymer. At least a portion of the purification solvent(s) in the solution thus formed can then be removed (e.g., by evaporation or distillation). Without wishing to be bound by theory, it is believed that this process can improve the purity of the final polymer solution by removal of residual water and polymerization solvent(s) with the purification solvent(s) (e.g., by evaporation or distillation). Further, without wishing to be bound by theory, it is believed that adding the purification solvent(s) in this step can prevent the polymer from precipitation out of the solution during the solvent removal process.

The distillation conditions can be any temperature and pressure under which the polymer is stable that will produce the desired end result. In some embodiments, the distillation temperature is from about 20° C. to about 70° C. (e.g., from about 25° C. to about 45° C.). In some embodiments, the distillation pressure is from about 760 Torr to about 0.1 Torr (e.g., from about 100 Torr to about 0.1 Torr). While the process detailed above leads to PI and PAE polymers of enhanced purity, it should be noted that additional process steps including, but not limited to, ion exchange and filtration may be included before and/or after steps 3 and 4 in this process.

In some embodiments, this disclosure features a purified PI or PAE polymer solution obtained from the process above. In some embodiments, a purified PI or PAE polymer can be isolated from the purified polymer solution obtained above by any suitable method known in the art (e.g., by precipitation or removal of solvents via distillation).

In one embodiment, the PI and PAE polymers of enhanced purity produced using the process of the present disclosure can be incorporated into compositions (e.g., film-forming compositions, thermally curable compositions, photosensitive compositions).

In some embodiments, this disclosure features a process of preparing a film on a substrate (e.g., a semiconductor substrate). The process can include (a) providing an organic solution containing a polyimide or polyamic ester in at least one polar, aprotic polymerization solvent; (b) adding at least one purification solvent to the organic solution to form a diluted organic solution, the at least one purification solvent is less polar than the at least one polymerization solvent and has a lower water solubility than the at least one polymerization solvent at 25° C.; (c) washing the diluted organic solution with water or an aqueous solution to obtain a washed organic solution; (d) removing at least a portion of the at least one purification solvent in the washed organic solution to obtain a solution containing a purified polyimide or polyamic ester; and (e) coating the solution containing a purified polyimide or polyamic ester on a substrate to form a film.

In some embodiments, the coating step described above can be performed by ink jet printing, spin coating, spray coating, dip coating, roller coating, or dynamic surface tension coating.

In some embodiments, this disclosure features an article that includes a semiconductor substrate and a film formed by the process above on the semiconductor substrate. Examples of such articles include a wire isolation, a wire coating, a wire enamel, or an inked substrate. In some embodiments, this disclosure features a semiconductor device containing the article described above. For example, the semiconductor device can be an integrated circuit, a light emitting diode, a solar cell, and a transistor.

In some embodiments, this disclosure is directed to a process for producing a free-standing film from the purified PI or PAE polymer solutions described herein, as well as the free-standing film thus obtained. The process can include the following steps:

a) coating a substrate with a purified PI or PAE polymer solution described herein to form a film coated substrate,
b) baking the film coated substrate (e.g., in a first baking step at a temperature $T_1$) to remove at least a portion (e.g., substantially all) of the solvent in the purified PI or PAE polymer solution; and
c) releasing the film coating from the substrate (e.g., by applying a mechanical force or a chemical treatment) to obtain a free-standing film.

In some embodiments, $T_1$ can be less than about 150° C. Examples of suitable substrates that can be used in the above process include, but not limited to, semiconductor substrates such as a silicon oxide wafer (which can facilitate release of the film by using a HF treatment), various plastic carriers such as polyethylene terephthalate (PET) substrates (which is flexible and can be easily removed by peeling), ceramic, glass panel or flexible glass film, textiles films, metal foil or sheet (such as copper or aluminum sheet), paper and the like.

Optionally, additional treatment of the film, such as exposure to radiation, corona, plasma and/or microwave radiation or a second baking step at a temperature $T_2$ (e.g., from about 180° C. to about 250° C.) can be applied to cure the film coating after the first baking step and before releasing the film to become free-standing.

Optionally, additional treatments that can be applied to the free-standing film include, but not limited to, washing the free-standing film with water or solvent and/or drying the free-standing film.

An example of the mechanical force to remove the film includes, but not limited to, peeling. An example of a chemical treatment to release the film includes, but not limited to, a dilute aqueous HF solution treatment.

In some embodiments, once the free-standing film is formed, it can be applied to a semiconductor substrate suitable for use in semiconductor devices. Examples of such semiconductor substrates include printed circuit boards and flexible printed circuit boards.

The contents of all publications cited herein (e.g., patents, patent application publications, and articles) are hereby incorporated by reference in their entirety.

EXAMPLES

Abbreviation
6FDA: 2,2'-bis(3,4-dicarboxyphenyl)hexafluoropropane dianhydride
DAPI: 4,4'-[1,4-phenylene-bis(1-methylethylidene)] bisaniline
BTDA: 3,3',4,4'-benzophenone tetracarboxylic dianhydride
PMDA: Pyromellitic dianhydride
ODA: 4,4'-oxydianiline ODPA: 4,4'-oxydiphthalic anhydride
DAM: 1,3-diaminomesitylene
HEMA: Hydroxyethylmethacrylate
NMP: N-Methyl pyrrolidinone
GBL: Gamma-butyrolactone
DMSO: Dimethylsulfoxide Example 1

An example of a PI polymer was prepared using one diamine and one dianhydride where the isolation solvent (i.e., a lactone) was different from the purification solvents (i.e., an ester and a ketone). The ratio of water to polymer used was 46:1.

Solid 6FDA (334.0 g) was charged to a solution of DAPI (218.4 g) in NMP (2206 g) at room temperature. Additional NMP (816 g) was used to rinse the dianhydride into solution. The reaction temperature was increased to 60° C. and the mixture was allowed to react for 3.5 hours. Next, acetic anhydride (125.7 g) and pyridine (49.5 g) were added, the reaction temperature was increased to 100° C., and the mixture was allowed to react for 12 hours.

The reaction mixture was cooled to room temperature and transferred to a larger vessel equipped with a mechanical stirrer. The reaction solution was diluted using ethyl acetate as a purification solvent and washed with water for one hour. Stirring was stopped and the mixture was allowed to stand undisturbed. Once phase separation had occurred, the aqueous phase was removed. The organic phase was diluted using a combination of ethyl acetate and acetone as purification solvents and washed three more times with water. The amounts of purification solvents (i.e., ethyl acetate and acetone) and water used in all of the washes are shown in Table 1.

TABLE 1

| | Wash 1 | Wash 2 | Wash 3 | Wash 4 |
|---|---|---|---|---|
| Ethyl Acetate (g) | 4085 | 1897 | 1025 | 1030 |
| Acetone (g) | — | 696 | 570 | 570 |
| Water (g) | 5311 | 6585 | 6580 | 6700 |

The washed organic phase was concentrated by vacuum distillation. GBL (705 g) was added as an isolation solvent and vacuum distillation was continued. The final polymer solution had a concentration of 33.82 wt %. Upon GC analysis, there was no detectable NMP in the final polymer solution.

Example 2

An example of an end-capped PI polymer was prepared using one diamine and one dianhydride where the isolation solvent (i.e., a lactone) was different from the purification solvents (i.e., an ester and a ketone). The ratio of the aqueous washing solution to polymer used was 48:1.

Solid 6FDA (244.3 g) was charged to a solution of DAPI (159.8 g) in NMP (2290 g) at room temperature. The reaction temperature was increased to 60° C. and the mixture was allowed to react for 3 hours. Next, 7-oxabicyclo[2.2.1]hept-5-ene-2,3-dicarboxylic anhydride (16.7 g) was added to the reaction mixture. After an additional 3 hours at 60° C., acetic anhydride (92.0 g) and pyridine (36.2 g) were added, the reaction temperature was increased to 100° C., and the mixture was allowed to react for 12 hours.

The reaction mixture was cooled to room temperature and transferred to a larger vessel equipped with a mechanical stirrer. The reaction solution was diluted using ethyl acetate as a purification solvent and washed with a 1% solution of aqueous hydrochloric acid for one hour. Stirring was stopped and the mixture was allowed to stand undisturbed. Once phase separation had occurred, the aqueous phase was removed. The organic phase was diluted using a combination of ethyl acetate and acetone as purification solvents and washed three times with water. The amounts of purification solvents (i.e., ethyl acetate and acetone) and water used in all of the washes are shown in Table 2.

TABLE 2

|                  | Wash 1 | Wash 2 | Wash 3 | Wash 4 |
|------------------|--------|--------|--------|--------|
| Ethyl Acetate (g)| 3111   | 1447   | 778    | 780    |
| Acetone (g)      | —      | 527    | 429    | 440    |
| 1% Aqueous HCl (g)| 4045  | —      | —      | —      |
| Water (g)        | —      | 5015   | 5009   | 5014   |

The washed organic phase was concentrated by vacuum distillation. GBL was added as an isolation solvent and vacuum distillation was continued. The final polymer solution had a concentration of 41.99 wt %. Upon GC analysis, there was no detectable NMP in the final polymer solution.

Example 3

An example of an end-capped PI polymer was prepared using one diamine and one dianhydride where the isolation solvent (i.e., a lactone) was different from the purification solvents (i.e., an ester and a ketone). The ratio of water to polymer used was 48:1.

Solid 6FDA (333.9 g) was charged to a solution of DAPI (218.4 g) in NMP (2721 g) at room temperature. Additional NMP (410 g) was used to rinse the dianhydride into solution. The reaction temperature was increased to 60° C. and the mixture was allowed to react for 5 hours. Next, 7-oxabicyclo[2.2.1]hept-5-ene-2,3-dicarboxylic anhydride (22.8 g) and NMP (21.8 g) were added to the reaction mixture. After an additional 3 hours at 60° C., acetic anhydride (126.6 g) and pyridine (48.9 g) were added, the reaction temperature was increased to 100° C., and the mixture was allowed to react for 12 hours.

The reaction mixture was cooled to room temperature and transferred to a larger vessel equipped with a mechanical stirrer. The reaction solution was diluted with ethyl acetate as a purification solvent and washed with water for one hour. Stirring was stopped and the mixture was allowed to stand undisturbed. Once phase separation had occurred, the aqueous phase was removed. The organic phase was diluted with a combination of ethyl acetate and acetone as purification solvents and washed three more times with water. The amounts of purification solvents (i.e., ethyl acetate and acetone) and water used in all of the washes are shown in Table 3.

TABLE 3

|                  | Wash 1 | Wash 2 | Wash 3 | Wash 4 |
|------------------|--------|--------|--------|--------|
| Ethyl Acetate (g)| 4237   | 1967   | 1061   | 1057   |
| Acetone (g)      | —      | 724    | 586    | 589    |
| Water (g)        | 5508   | 6820   | 6817   | 6822   |

The washed organic phase was concentrated by vacuum distillation. GBL (706 g) was added as an isolation solvent and vacuum distillation was continued. The final polymer solution had a concentration of 43.75 wt %. The NMP content of the final polymer solution was determined by GC to be 0.05 wt % of the polymer.

Example 4

An example of an end-capped PI polymer was prepared using two diamines and one dianhydride where the isolation solvent (i.e., a ketone) was the same as one of the purification solvents (i.e., a ketone and an aromatic hydrocarbon). The ratio of water to polymer used was 21:1.

A solution of DAPI (160 g) and DAM (90.2 g) in NMP (667 g) was added slowly by addition pump to a slurry of BTDA (367.3 g) in NMP (772.8 g) at 50° C. When addition was complete, the reaction temperature was increased to 60° C. and the mixture was allowed to react for 18 hours. Next, solid 5-isobenzofurancarboxylic acid, 1,3-dihydro-1,3-dioxo-2-[(2-methyl-1-oxo-2-propen-1-yl)oxy]ethyl ester (36.6 g) and NMP (205 g) were added to the reaction mixture. After an additional 6 hours at 60° C., pyridine (47.7 g) and NMP (180 g) were added. After an additional 18 hours at 60° C., acetic anhydride (122.4 g) was added, the reaction temperature was increased to 100° C., and the mixture was allowed to react for 12 hours.

The reaction mixture was cooled to room temperature and 303.5 g of the mixture was transferred to a separatory flask equipped with a mechanical stirrer. The reaction solution was diluted with cyclopentanone and toluene as purification solvents and washed with water for one hour. Stirring was stopped and the mixture was allowed to stand undisturbed. Once phase separation had occurred, the aqueous phase was removed. The organic phase was diluted with cyclopentanone as a purification solvent and washed three more times with water. The amounts of purification solvents (i.e., cyclopentanone and toluene) and water used in all of the washes are shown in Table 4.

TABLE 4

|                  | Wash 1 | Wash 2 | Wash 3 | Wash 4 |
|------------------|--------|--------|--------|--------|
| Toluene (g)      | 306.3  | —      | —      | —      |
| Cyclopentanone (g)| 599.3 | 124.5  | 99.3   | 102.8  |
| Water (g)        | 605.0  | 401.6  | 403.7  | 402.1  |

The washed organic phase was concentrated by vacuum distillation. Cyclopentanone (300.6 g) was added as an isolation solvent and vacuum distillation was continued. The final polymer solution had a concentration of 33.92 wt %. The NMP content of the final polymer solution was determined by GC to be 0.29 wt % of the polymer.

Example 5

An example of an end-capped PI polymer was prepared using two diamines and two dianhydrides where the isolation solvent (i.e., a ketone) was the same as one of the purification solvents (i.e., a ketone and an aromatic hydrocarbon). The ratio of water to polymer used was 20:1.

A solution of DAPI (199.8 g) and DAM (112.7 g) in NMP (574 g) was added slowly by addition pump to a slurry of BTDA (221.5 g) and PMDA (150.0 g) in NMP (1022.5 g) at room temperature. When addition was complete, additional NMP (455 g) was added, the reaction temperature was increased to 60° C., and the mixture was allowed to react for 18 hours. Next, solid 5-isobenzofurancarboxylic acid, 1,3-dihydro-1,3-dioxo-2-[(2-methyl-1-oxo-2-propen-1-yl)oxy]ethyl ester (76.1 g) and NMP (59 g) were added to the reaction mixture. After an additional 20 hours at 60° C., acetic anhydride (153.4 g) and pyridine (60.1 g) were added, the reaction temperature was increased to 100° C., and the mixture was allowed to react for 15 hours.

The reaction mixture was cooled to room temperature and 414.4 g of the mixture was transferred to a separatory flask equipped with a mechanical stirrer. The reaction solution was diluted using cyclopentanone and toluene as purification solvents and washed with water for one hour. Stirring was stopped and the mixture was allowed to stand undisturbed. Once phase separation had occurred, the aqueous phase was removed. The organic phase was diluted with cyclopentanone as a purification solvent and washed three more times with water. The amounts of purification solvents (i.e., cyclopentanone and toluene) and water used in all of the washes are shown in Table 5.

TABLE 5

|  | Wash 1 | Wash 2 | Wash 3 | Wash 4 |
|---|---|---|---|---|
| Toluene (g) | 410.5 | — | — | — |
| Cyclopentanone (g) | 639.5 | 90.7 | 99.4 | 100.2 |
| Water (g) | 612.1 | 600.9 | 402.5 | 400.8 |

(i.e., cyclopentanone and toluene) and water used in all of the washes are shown in Table 6.

TABLE 6

|  | Wash 1 | Wash 2 | Wash 3 | Wash 4 | Wash 5 |
|---|---|---|---|---|---|
| Toluene (g) | 96.5 | — | — | — | — |
| Cyclopentanone (g) | 99.6 | 65.2 | 43.3 | 44.7 | 25.9 |
| Water (g) | 177.0 | 175.1 | 154.7 | 161.8 | 140.5 |

A portion of the washed organic phase was concentrated by vacuum distillation. Cyclopentanone (179.7 g) was added as an isolation solvent and vacuum distillation was continued. The final polymer solution had a concentration of 8.86 wt %. Upon GC analysis, there was no detectable NMP in the final polymer solution.

The reagents used and the properties of the polymers obtained in Examples 1-6 are summarized in Table 7.

TABLE 7

| | SOLUBLE POLYIMIDE POLYMER DATA | | | | | |
|---|---|---|---|---|---|---|
| Polymer | Example 1 | Example 2 | Example 3 | Example 4 | Example 5 | Example 6 |
| Diamine(s) | DAPI | DAPI | DAPI | DAPI:DAM | DAPI:DAM | ODA |
| Dianhydride(s) | 6FDA | 6FDA | 6FDA | BTDA | BTDA:PMDA | 6FDA |
| Molecular Weight | 14900 | 25000 | 24000 | 25700 | 13100 | 15400 |
| PDI | 2.3 | 2.8 | 2.8 | 2.8 | 2.5 | 2.2 |
| Solids (Wt %) | 33.82 | 41.99 | 43.75 | 33.92 | 31.23 | — |
| NMP Content (Wt %) | ND | ND | 0.05 | 0.29 | 0.4 | ND |

ND: Not detectable.

The washed organic phase was concentrated by vacuum distillation. Cyclopentanone (378.5 g) was added as an isolation solvent and vacuum distillation was continued. The final polymer solution had a concentration of 31.23 wt %. The NMP content of the final polymer solution was determined by GC to be 0.40 wt % of the polymer.

Example 6

An example of a non-end-capped PI polymer was prepared using one diamine and one dianhydride where the isolation solvent (i.e., a lactone) was different from the purification solvents (i.e., an ester and a ketone). The ratio of water to polymer used was 46:1.

Solid 6FDA (81.52 g) was charged to a solution of ODA (40.10 g) in NMP (539.7 g) at room temperature. Additional NMP (146 g) was used to rinse the dianhydride into solution. The reaction temperature was increased to 60° C. and the mixture was allowed to react for 4 hours. Next, acetic anhydride (32.32 g) and pyridine (12.00 g) were added, the reaction temperature was increased to 100° C., and the mixture was allowed to react for 12 hours.

The reaction mixture was cooled to room temperature and 96.1 g was transferred to a separatory funnel. The reaction solution was diluted using cyclopentanone and toluene as purification solvents and washed with water by inverting the funnel twenty times. The mixture was allowed to stand undisturbed until two separate and distinct layers were formed. Once phase separation had occurred, the aqueous phase was removed. The organic phase was diluted using cyclopentanone as a purification solvent and washed four more times with water. The amounts of purification solvents Example 7

An example of a PAE polymer was prepared using one diamine and one dianhydride where the isolation solvents (i.e., a lactone and a sulfoxide) were different from the purification solvents (i.e., an ester and a ketone). The ratio of water to polymer used was 69:1.

In a 5-L jacketed vessel, HEMA (108.72 g) was added to a slurry of ODPA (126.65 g), hydroquinone (0.22 g) and pyridine (143.56 g) in diglyme (691 g) at room temperature. The reaction mixture was heated to 70° C. for 4 hours and then cooled to −10° C. A solution of thionyl chloride (100.97 g) in diglyme (369 g) was slowly added to the reaction mixture at −10° C. The reaction mixture was warmed to 0° C. for 1 hour and then re-cooled to −10° C. NMP (312 g) was added to the reaction mixture followed by slow addition of a solution of ODA (483.23 g) in NMP (74.4 g). Following addition of ODA, the reaction mixture was warmed to 0° C. for 30 minutes and then warmed to 10° C. Anhydrous ethanol (452.5 g) was added and the reaction mixture warmed to room temperature.

A portion of the reaction mixture (523.2 g) was transferred to a separatory flask equipped with a mechanical stirrer. The reaction solution was diluted with cyclopentanone and ethyl acetate as purification solvents and washed with water for one hour. Stirring was stopped and the mixture was allowed to stand undisturbed. Once phase separation had occurred, the aqueous phase was removed. The organic phase was diluted with cyclopentanone as a purification solvent and washed three more times with water. The amounts of purification solvents (i.e., cyclopentanone and ethyl acetate) and water used in all of the washes are shown in Table 8.

TABLE 8

|  | Wash 1 | Wash 2 | Wash 3 | Wash 4 |
|---|---|---|---|---|
| Ethyl Acetate (g) | 520.4 | — | — | — |
| Cyclopentanone (g) | 237.2 | 154.0 | 162.3 | 168.0 |
| Water (g) | 877.3 | 876.0 | 877.7 | 880.5 |

The washed organic phase was concentrated by vacuum distillation. A 80:20 mixture of GBL:DMSO (59.4 g) was added as isolation solvents and vacuum distillation was continued. The final polymer solution had a concentration of 44.68 wt %.

The NMP content of the purified polymer was determined by GC to be 4.29 wt % of the polymer. Although the process described in Example 7 for purifying a PAE polymer has not been optimized, the above results show that it can reduce the residual amount of the polymerization solvent (i.e., NMP) to a level much lower than that obtained by Comparative Example 1 (i.e., 6.15 wt %), which describes a conventional precipitation method for purifying the same PAE polymer.

Comparative Example 1

A portion of the reaction mixture produced in Example 7 was purified by a conventional method as follows. The ratio of water to polymer used was 492:1.

The PAE polymerization solution (2997 g) was slowly added to water (36.0 kg) to precipitate the crude polymer. The crude polymer was isolated by vacuum filtration, washed with water (28.8 kg) and dried under vacuum. The crude dry polymer (131 g) was dissolved in THF (750 g) in a glass bottle, water (80 g) was added and the solution mixed by rolling for 1 hour. UP6040 ion exchange resin (131 g) was added, and the mixture rolled overnight. The mixture was filtered to remove ion exchange resin and the filtrate was slowly added to water (12.0 kg) to re-precipitate the polymer. The solid polymer was collected by vacuum filtration, washed with water (9.6 kg) and dried under vacuum at 45° C. overnight. The NMP content of the final precipitated polymer was determined by GC to be 6.15 wt % of the polymer.

GPC analysis of the final solid polymer produced by the convention method with the polymer solution produced in Example 7 are provided in FIG. 1, which shows that the molecular weight profiles of the polymers were identical. Table 9 summarizes the differences between the processes used and the polymers obtained in Example 7 and Comparative Example 1.

TABLE 9

PROCESS COMPARISON: EXAMPLE 7 AND COMPARATIVE EXAMPLE 1

| Example | Comparative Example 1 | Example 7 | Unit |
|---|---|---|---|
| Molecular Weight | 31200 | 31900 | Daltons |
| PDI | 2.4 | 2.4 |  |
| Water Used | 492 | 69 | kg/kg of Polymer |
| IEX Needed | Yes | No |  |

As shown in Table 9, the process described in Example 7 can significantly reduce the amount of water used and thereby generate significantly less waste compared to the conventional precipitation process described in Comparative Example 1.

Comparative Example 2

A portion of the reaction mixture produced in Example 4 was purified by a conventional method as follows.

A portion of the PI polymerization solution (100 g) was diluted with an equal volume of THF and the diluted solution was slowly added to water (2000 g) to precipitate the crude polymer. The crude polymer was isolated by vacuum filtration and washed with water. The crude wet polymer was slurried with methanol, collected by vacuum filtration and dried under vacuum at 45° C. overnight.

The NMP content of the final precipitated polymer was determined by GC to be 2.25 wt % of the polymer.

Comparative Example 3

A portion of the reaction mixture produced in Example 6 was purified by a conventional method as follows.

A portion of the PI polymerization solution (10 g) was diluted with an equal volume of THF and the diluted solution was slowly added to water (200 g) to precipitate the crude polymer. The crude polymer was isolated by vacuum filtration and washed with water. The crude wet polymer was slurried with methanol, collected by vacuum filtration and dried under vacuum at 45° C. overnight.

The NMP content of the final precipitated polymer was determined by GC to be 6.08 wt % of the polymer.

Composition and Film Example 1 (A Film Forming Composition)

A mixture containing 100 parts of the polymer solution obtained in Example 1 and 1.5 part of (3-triethoxysilyl) propyl succinic anhydride are prepared and filtered by using a 1.0 micron filter. The composition is spin coated on a silicon wafer to form a coating with a thickness of 10 microns. The coated wafer is baked at 120° C. for 3 minutes. Coating defects and film cracking are checked by optical microscope.

Composition and Film Example 2 (A Film Forming, Thermally-curable Composition)

A thermosetting composition is prepared by mixing 100 parts of the polymer solution obtained in Example 2, 8.5 parts of dipentaerythritol hexakis (3-mercaptopropionate), 0.5 parts of N-methyldicyclohexyl amine, and 4.5 part of gamma-glycidoxypropyltriethoxysilane. The composition is filtered by using a 1.0 micron filter. The composition is spin coated on a silicon wafer to form a coating with a thickness of 10 microns. The coated wafer is baked at 125° C. for 5 minutes. Coating defects and film cracking are checked by optical microscope. The film is heated under $N_2$ atmosphere in a convection oven at 200° C. for 1 hour. The resulting film is again checked by optical microscope for film defects. The film is immersed in various solvents (PGMEA, GBL, and acetone) to evaluate its solvent resistance.

Composition and Film Example 3 (A Film Forming, Thermally-curable Composition)

A thermosetting composition is prepared by mixing 100 parts of the polymer solution obtained in Example 3, 7 parts of trimethylolpropane tris(4-sulfanylcyclohexanecarboxylate), 0.7 parts of triethylamine, and 3 part of (3-triethoxysilylpropyl)-t-butyl carbamate. The composition is filtered by using a 1.0 micron filter. The composition is spin coated on a silicon wafer to form a coating with a thickness of 12 microns. The coated wafer is baked at 130° C. for 4 minutes. Coating defects and film cracking are checked by optical microscope. The film is heated under $N_2$ atmosphere in a convection oven at 220° C. for 1 hour. The resulting film is checked again by optical microscope for film defects. The film is immersed in various solvents (PGMEA, GBL, and acetone) to evaluate its solvent resistance.

Composition and Film Example 4 (A Film Forming, Photosensitive Composition)

A photosensitive composition is prepared by mixing 100 parts of the polymer solution obtained in Example 4, 20 parts of tetraethyleneglycol dimethacrylate and 1.5 parts of NCI-831 (trade name, available from ADEKA Corporation). The composition is filtered by using a 0.2 micron filter and is spin coated on a silicon wafer to form a coating with a thickness of about 9 microns. The coated wafer is baked at 105° C. for 3 minutes. The photosensitive polyimide film is exposed with a broadband UV exposure tool (Carl Süss MA-56) through a mask having a desired pattern for exposure.

After the exposure, unexposed portions are removed by using cyclopentanone as developer followed by rinsing the developed film with PGMEA to form a pattern. After pattern formation, the developed film is heated at a temperature of 100° C. for a time period of 2 minutes. The resulting film is checked by optical microscope for film defects.

What is claimed is:

1. A process of purifying a polymer, comprising:
providing an organic solution containing a polyimide or polyamic ester in at least one polar, aprotic polymerization solvent;
adding at least one purification solvent to the organic solution to form a diluted organic solution, the at least one purification solvent is less polar than the at least one polymerization solvent and has a lower water solubility than the at least one polymerization solvent at 25° C.;
washing the diluted organic solution with water or an aqueous solution, the washing comprises mixing the diluted organic solution with water or an aqueous solution to form a mixture having an organic phase and an aqueous phase, and removing the aqueous phase to obtain a washed polymer-containing organic solution; and
removing a portion of the at least one purification solvent in the washed polymer-containing organic solution to obtain a solution containing a purified polyimide or polyamic ester;
wherein the process avoids precipitation of the polyimide or polyamic ester.

2. The process of claim 1, wherein the at least one polymerization solvent comprises dimethylformamide, dimethylacetamide, N-formylmorpholine, N-methylpyrrolidinone, N-ethylpyrrolidinone, dimethylsulfoxide, gamma-butyrolactone, hexamethyl phosphoric acid triamide, tetrahydrofuran, methyltetrahydrofuran, or 1,4-dioxane.

3. The process of claim 1, wherein the at least one polymerization solvent comprises at least one water miscible solvent.

4. The process of claim 1, wherein the at least one purification solvent comprises an ester, an ether, a ketone, or a hydrocarbon optionally substituted by at least one halide.

5. The process of claim 4, wherein the least one purification solvent comprises methyl acetate, ethyl acetate, n-propyl acetate, isopropyl acetate, n-butyl acetate, isobutyl acetate, sec-butyl acetate, cyclohexyl acetate, ethyl lactate, propylene glycol monomethyl ether acetate, tetrahydrofurfuryl acetate, propyl formate, butyl formate, isobutyl formate, pentyl formate, ε-caprolactone, diethyl ether, dipropyl ether, dibutyl ether, dicyclohexyl ether, cyclopentyl methyl ether, methyl tert-butyl ether, ethyl tert-butyl ether, anisole, phenyl ethyl ether, diphenyl ether, 1,2-dimethoxypropane, 1,2-dimethoxyethane, 2-butanone, 2-pentanone, 3-pentanone, methyl isobutyl ketone, ethyl isobutyl ketone, methyl isopropyl ketone, cyclopentanone, cyclohexanone, acetophenone, isophorone, mesityl oxide, benzene, toluene, xylene, ethyl benzene, chlorobenzene, 1,2-dichlorobenzene, α,α,α-trifluorotoluene, pentane, hexane, heptane, octane, cyclohexane, methylcyclohexane, or cyclohexene.

6. The process of claim 1, wherein the least one purification solvent comprises at least one water immiscible solvent.

7. The process of claim 1, wherein adding at least one purification solvent further comprises adding at least one purification co-solvent that has a water solubility higher than the at least one purification solvent.

8. The process of claim 7, wherein the at least one purification co-solvent comprises acetone, gamma-butyrolactone, furan, tetrahydrofuran, methyl tetrahydrofuran, tetrahydrofurfuryl methyl ether, or 1,4-dioxane.

9. The process of claim 8, wherein the at least one purification co-solvent comprises at least one water miscible solvent.

10. The process of claim 1, wherein the aqueous solution comprises an acid or a base.

11. The process of claim 1, wherein washing the diluted organic solution substantially removes the at least one polymerization solvent or another impurity in the diluted organic solution.

12. The process of claim 1, wherein the process further comprises adding at least one isolation solvent to the washed polymer-containing organic solution before removing at least a portion of the at least one purification solvent.

13. The process of claim 12, wherein the at least one isolation solvent has a boiling point higher than a boiling point of the at least one purification solvent.

14. The process of claim 12, wherein the at least one isolation solvent comprises a ketone, an ester, a hydrocarbon, a sulfoxide, or an ether.

15. The process of claim 14, wherein the at least one isolation solvent comprises methyl ethyl ketone, methyl isobutyl ketone, 2-heptanone, cyclopentanone, cyclohexanone, xylene, gamma-butyrolactone, dimethylsulfoxide, propylene glycol monomethyl ether acetate, propylene glycol monomethyl ether, or ethyl lactate.

16. The process of claim 12, wherein the at least one isolation solvent is different from the at least one purification solvent.

17. The process of claim 12, wherein the at least one isolation solvent is the same as the at least one purification solvent.

18. The process of claim 1, wherein the portion of the at least one purification solvent is removed by evaporation or distillation.

19. The process of claim 1, wherein the organic solution containing a polyimide or polyamic ester in at least one polar, aprotic polymerization solvent is obtained from a polymerization reaction without isolating the polyimide or polyamic ester.

20. The process of claim 1, further comprising concentrating the solution containing a purified polyimide or polyamic ester after the removing step.

* * * * *